(12) United States Patent
Sera

(10) Patent No.: US 8,318,155 B2
(45) Date of Patent: Nov. 27, 2012

(54) NUCLEIC ACID CLEAVING AGENT

(75) Inventor: Takashi Sera, Kyoto (JP)

(73) Assignee: Kyoto University, Kyoto (JP)

( * ) Notice: Subject to any disclaimer, the term of this patent is extended or adjusted under 35 U.S.C. 154(b) by 544 days.

(21) Appl. No.: 12/281,829

(22) PCT Filed: Mar. 7, 2007

(86) PCT No.: PCT/JP2007/055016
§ 371 (c)(1),
(2), (4) Date: Dec. 22, 2008

(87) PCT Pub. No.: WO2007/102618
PCT Pub. Date: Sep. 13, 2007

(65) Prior Publication Data
US 2012/0164125 A1 Jun. 28, 2012

(30) Foreign Application Priority Data

Mar. 8, 2006 (JP) ................. 2006-063061

(51) Int. Cl.
*A61K 38/46* (2006.01)
*C12N 9/22* (2006.01)
*C12N 9/14* (2006.01)
*C12N 15/00* (2006.01)
*C12N 1/20* (2006.01)
*C12P 21/06* (2006.01)
*C12P 19/34* (2006.01)

(52) U.S. Cl. ...... 424/94.6; 435/199; 435/195; 435/69.1; 435/91.1; 435/320.1; 435/455; 435/252.3; 536/23.1; 536/23.2

(58) Field of Classification Search .............. 424/94.6; 435/199, 195, 69.1, 91.1, 320.1, 455, 252.3; 536/23.1, 23.2
See application file for complete search history.

(56) References Cited

U.S. PATENT DOCUMENTS
2003/0134350 A1* 7/2003 Sera ............................. 435/69.1
2004/0091878 A1* 5/2004 Sera ................................. 435/6

FOREIGN PATENT DOCUMENTS
| JP | 2002-505111 | 2/2002 |
| JP | 2004-519211 | 7/2004 |
| JP | 2005-143484 | 6/2005 |
| WO | 99/45132 | 9/1999 |
| WO | 02/08286 A2 | 1/2002 |

OTHER PUBLICATIONS

Durai et al., Zinc finger nucleases: custom-designed molecular scissors for gene enginerring of plant and mammalian cells. Nuc. Acids Res., 2005, vol. 33 (18): 5978-5990.*
Mani et al., Design, engineering, and characterization of zinc finger nucleases. Biochem. Biophys. Res. Commun., 2005, vol. 335: 447-457.*
Porteus et al., Gene targeting using zinc finger nucleases. Nat. Biotechnol., 2005, vol. 23 (8): 967-973.*
Couzin et al., As Gelsinger case ends, Gene therapy suffers another blow. Science, 2005, vol. 307: 1028.*
Wolf JA., The "grand" problem of synthetic delivery. Nat. Biotechnol., 2002, vol. 20: 768-769.*
Rosenberg et al., Gene therapist, heal thyself. Science, 2000, vol. 287: 1751.*
Donsante et al., AAV vector integration sites in mouse hepatocellular carcinoma. Science, 2007. vol. 317: 477.*
Touchette et al., Gene therapy: Not ready for prime time. Nat. Med., 1996, vol. 2(1): 7-8.*
Raper SE., Gene therapy: The good, the bad, and the ugly. Surgery, 2005, vol. 137(5): 487-492.*
Kimmelman J., Recent developments in gene transfer: risk and ethics. BMJ, 2005, vol. 350; 79-82.*
Juengst ET., What next for human gene therapy? BMJ., 2003, vol. 326: 1410-1411.*
Cameron ER., Recent advances in transgenic technology. 1997, vol. 7: 253-265.*
Kappel et al., Regulating gene expression in transgenic animals. Current Opinion in Biotechnology 1992, vol. 3: 548-553.*
Mullins et al., Transgenesis in nonmurine species. Hypertension, 1993, vol. 22 (4): 630-633.*
Mullins et al., Transgenesis in the rat and larger mammals. J. Clin. Invest., 1996, vol. 97 (7): 1557-1560.*
Wigley et al., Site-specific transgene insertion: an approach. Reprod. Fert. Dev., 1994, vol. 6: 585-588.*
Dubey et al., Metal complexes of 1,4,7-triazacyclononane and their oligonucleotide conjugates as chemical nucleases. Ukrainica Bioorganica Acta, 2007, vol. 1:11-19.*
Fleisher et al., Light-induced cleavage of DNA by metal complexes. Inorg. Chem., 1986, vol. 25 (20): 3549-3551.*
Ossipov et al., Synthesis of [Ru(phen)2dppz]2+-tethered oligo-DNA and studies on metallointercalation mode into the DNA complex. J. Am. Chem. Soc., 2001, vol. 123: 3551-3562.*
Zheltukhina et al., Synthesis and structure-function study of artificial nucleases on the basis of hemin conjugates with peptide fragments of cell differentiation factor HLDF. Russ. J. Bioorganic Chem., 2006, vol. 32 (2): 179-190.*
English Language Abstract of JP 2005-143484.
Kim et al. "Hybrid restriction enzymes: Zinc finger fusions to *Fok* I cleavage domain" *Proc. Natl. Acad. Sci. USA* 93:1156-1160, 1996.
Bibikova et al. "Enhancing Gene Targeting with Designed Zinc Finger Nucleases" *Science* 300:764, 2003.
Eisenstein, M. "Human genomic repair at your fingertips" *Nature Methods* 2(6):405, 2005; doi 10.1038/nmeth0605-405.
Mino et al. "Inhibition of DNA Replication of Human Papillomavirus by Artificial Zinc Finger Proteins" *J. Virol.* 80(1 1):5405-5412, 2006.
Dhanesekaran et al. "Designer Zinc Finger Proteins: Tools for Creating Artificial DNA-Binding Functional Proteins" *Acc. Chem. Res.* 39:45-52, 2006.

(Continued)

*Primary Examiner* — Ganapathirama Raghu
(74) *Attorney, Agent, or Firm* — Greenblum & Bernstein, P.L.C.

(57) ABSTRACT

A nucleic acid cleaving agent having a cleaving activity specific to a desired cleavage site in a nucleic acid such as large DNA, which comprises (1) a nucleic acid cleaving moiety, and (2) at least two zinc finger proteins bound to the nucleic acid cleaving moiety, wherein at least one of the zinc finger proteins can specifically bind to a nucleotide sequence located upstream from the target cleavage site, and at least one of the remaining zinc finger proteins can specifically bind to a nucleotide sequence located downstream from the target cleavage site.

18 Claims, 4 Drawing Sheets

OTHER PUBLICATIONS

Sera et al. "Rational Design of Artificial Zinc-Finger Proteins Using a Nondegenerate Recognition Code Table" *Biochemistry* 41:7074-7081, 2002.

Nakatsukasa et al., "Site-specific DNA cleavage by artificial zinc finger-type nuclease with cerium-binding peptide" *Biochemical and Biophysical Research Communications*, vol. 330, pp. 247-52, 2005.

Reply to International Search Report and Written Opinion of the International Search Authority for PCT/JP2007/055016, of which the instant application is the National Stage, submitted Jul. 12, 2007 (7 pages).

Japanese Office Action issued with respect to counterpart Japanese Application No. 2008-542543, dated Jul. 3, 2012.

* cited by examiner

Reaction buffer :
  50 mM Tris-HCl (pH 7.5)
  100 mM NaCl
  10 mM CaCl2
  5 μM AZP-SNase Temperature : 37°C
Period of reaction time : 30 min DNA : SNase = 2000 : 1

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtcgggacc gaaaacggt                                                    19

<210> SEQ ID NO 2
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 2
cgaaaacggt                                                              10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtcgggacc                                                              10

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atatgtatac tatgtatac                                                    19

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gttgcgggat                                                              10

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtcgggacg ttgcgggat                                                    19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atatgtatac atatgtatac                                                   20

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
ggtcgggacc atatgtatac atatgtatac gttgcgggat                                40

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgggtaccg ggcccccct cgaggtcgac                                            30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgtaaaacg acggccagtg agcgcgcgta                                           30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcacacagga aacagctatg accatgatta                                           30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcggccgct ctagaactag tggatccccc                                           30

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser Gly Gly Gly Gly Ser Gly
1               5                   10                  15

Gly Gly Gly Ser
            20

<210> SEQ ID NO 14
<211> LENGTH: 40
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 14
ggtcgggacc atatgtatac atatgtatac cgaaaacggt                            40
```

NUCLEIC ACID CLEAVING AGENT

TECHNICAL FIELD

The present invention relates to a nucleic acid cleaving agent. More specifically, the present invention relates to a nucleic acid cleaving agent that can recognize a specific nucleotide sequence on a genome and cleave the genome in a site-specific manner.

BACKGROUND ART

Discovery of restriction enzymes made gene cloning possible using recombinant DNA techniques. Genetic engineering has lead to the remarkable expansion of various industries and studies. Numerous restriction enzymes that can selectively cleave specific nucleotide sequences are known. These enzymes, essential tools for genetic engineering, are widely used for analysis of gene structures and the like.

For restriction enzymes, only naturally occurring restriction enzymes have been conventionally used, and gene recombination techniques using the naturally occurring restriction enzymes are limited to those targeting small DNAs such as plasmids. However, many DNAs are far larger than plasmids, and treating large DNA using conventionally-available restriction enzymes results in fragmentation due to cleavage at a considerably large number of sites, making desired gene recombination procedures impracticable. For this reason, it has been desired to provide a means for freely manipulating large DNA. In particular, it has been desired to provide a restriction enzyme that can selectively cleave a specific nucleotide sequence in a large DNA molecule.

For example, Japanese Patent Unexamined Publication (Kokai) No. 2005-143484 discloses a method of allowing two peptide nucleic acids (PNAs) to invade into DNA to activate a phosphodiester bond at a desired site in the DNA and then adding a Ce(IV)-EDTA complex to cleave the nucleic acid in an active site (hot spot)-selective manner. In the above method, sequences and lengths of the PNAs used for the formation of the hot spot are not limited, and therefore, it is considered that DNA of any size can be precisely cleaved at a desired site. However, no practical example of desired intracellular cleavage was demonstrated.

Fusion proteins are known in which an enzyme, or enzyme active site that has a nucleic acid cleaving activity, is bound to a DNA-binding protein such as a zinc finger protein (ZEP). For example, a fusion protein in which a zinc finger protein is bound to a catalytically-active site of the restriction enzyme FokI was presented by Kim et al. (Kim, Y., et al., Proc. Natl. Acad. Sci. USA, 93, pp. 1156-1160, 1996). Bibikova et al. reported homologous recombination in cells of frog, *Drosophila* and human using a chimeric zinc finger nuclease (ZFN) (Bibikova M., et al., Science, 300, p. 764, 2003). For ZFN, it can be directed to cleave different target sites by replacing a zinc finger domain with another domain having different specificity. Ideally, this nuclease can therefore be designed to target any arbitrary sequence on a genome (Nature Methods 2, 405 (2005), doi: 10.1038/nmeth0605-405).

However, to cleave a nucleic acid using the aforementioned ZFN, two ZFN molecules need to act in a cooperative manner. That is, the two ZFN molecules bind oppositely to a desired site on a DNA and a double-stranded DNA is nicked, and then homologous recombination occurs between a chromosome and a donor DNA molecule to cause replacement with a desired nucleotide sequence. Therefore, for example, when a long region of a DNA chain is removed for gene therapy or the like, a problem arises that a set of two ZFN molecules is needed for each of two cleavage sites to perform homologous recombination. The ZFN molecule has a structure in which an enzyme cleavage site is bound to an end of a zinc finger protein (including a zinc finger protein having three, four, or six zinc finger domains). This molecule will not reduce affinity for a target site after the cleavage of a nucleic acid and remains bound to the nucleic acid. Therefore, the molecule fails to catalytically exert the cleavage action by repeating a cycle of binding and successive cleavage, followed by dissociation and rebinding.

DISCLOSURE OF THE INVENTION

An object of the present invention is to provide a nucleic acid cleaving agent having a cleaving activity specific to a desired cleavage site existing in large DNA or RNA molecules. More specifically, the object of the present invention is to provide a nucleic acid cleaving agent wherein a single molecule can solely and effectively cleave a desired cleavage site and can act catalytically, thus avoiding the aforementioned problems of ZFN.

To achieve the foregoing object, the inventors of the present invention designed a nucleic acid cleaving agent in which at least two independent zinc finger proteins (for example, zinc finger proteins each having three zinc fingers) are bound to a nucleic acid cleaving moiety, so that at least one of the zinc finger proteins binds upstream from a target cleavage site, and at least one of the remaining zinc finger proteins binds downstream from the target cleavage site. This nucleic acid cleaving agent strongly binds to a nucleic acid by at least two zinc finger proteins (for example, by two zinc finger proteins each comprising three zinc finger domains, namely by six zinc fingers in total) before cleavage of the nucleic acid. After the cleavage of the nucleic acid, each zinc finger protein is bound to one of two separate nucleic acids (the cleaved fragments). This configuration results in substantial decrease in the affinity of the agent for the nucleic acid compared to the affinity prior to the cleavage and allows easy dissociation of the agent from the nucleic acid after the cleavage. Using a nucleic acid cleavage agent of the invention in a nucleic acid cleavage reaction with significant excess of nucleic acid relative to the agent, the present inventors successfully cleaved a nucleic acid more efficiently than a fusion protein such as ZFN bound with a nucleic acid cleaving moiety at an end of a zinc finger protein under the same condition. Without being bound to a mechanism, the high nucleic acid cleaving activity of the present invention appears attributable to repeated turnover of nucleic acid cleavage activity by the nucleic acid cleaving agent of the invention.

The present invention thus provides a nucleic acid cleaving agent capable of specifically cleaving a target cleavage site in a nucleic acid which comprises (1) a nucleic acid cleaving moiety, and (2) at least two zinc finger proteins bound to the nucleic acid cleaving moiety, wherein at least one of the zinc finger proteins is capable of specifically binding to a nucleotide sequence located upstream from the target cleavage site, and at least one of the remaining zinc finger proteins is capable of specifically binding to a nucleotide sequence located downstream from the target cleavage site.

In preferred embodiments of the invention, the nucleic acid cleaving agent, has two zinc finger proteins bound to the nucleic acid cleaving moiety. In one embodiment, the total number of zinc finger domains between the two zinc finger proteins is from 4 to 8, and preferably from 5 to 7 domains. In another preferred embodiment, the nucleic acid cleaving agent of the invention has two zinc finger proteins, each with four or less zinc finger domains, and more preferably where each zinc finger protein three zinc finger domains.

Further, according to other preferred embodiments, the nucleic acid cleaving agent of the invention comprises zinc finger proteins bound to the nucleic acid cleaving moiety by means of a linker. In an embodiment with two zinc finger proteins, the nucleic acid cleaving agent has each two zinc finger proteins bound to the nucleic acid cleaving moiety by a peptide linker. Each peptide linker can independently be an oligopeptide linker, each independently containing 5 to 50 amino acid residues. In yet other preferred embodiments, the nucleic acid cleaving agent has a the nucleic acid cleaving moiety wherein that moiety is a nucleic acid cleaving enzyme, a nucleic acid cleaving domain thereof or a metal complex having a nucleic acid cleaving activity. In a another preferred embodiment, the nucleic acid cleaving moiety of the nucleic acid cleaving agent is Staphylococcal nuclease (SNase) or a nucleic acid cleaving domain thereof. The preferred target of the aforementioned nucleic acid cleaving agent is DNA, including genomic DNA, chromosomal DNA and large viral DNA.

Another aspect of the present invention provides nucleic acids encoding the nucleic acid cleaving agents of the invention, recombinant vectors, especially expression vectors, comprising those nucleic acids, host cells comprising the recombinant expression vectors of the invention and methods of producing the nucleic acid cleavage agent by culturing those host cells for a time and under conditions to express the agent and recovering the nucleic acid cleaving agent. The nucleic acids and recombinant vectors can be DNA or RNA, and preferably the recombinant vector can express the nucleic acid cleaving agent in a mammal.

Yet another aspect of the invention is directed to a method of site-specifically cleaving a nucleic acid by reacting a nucleic acid having a target cleavage site with a nucleic acid cleavage agent of the invention, the agent being specific for the desired target cleavage site, for a time and under conditions to cleave that site. The reaction, preferably, proceeds catalytically. In certain embodiments, the target cleavage site is a unique site on a genomic DNA or other large DNA or RNA.

Still other aspects of the invention are directed to methods of using the nucleic cleaving agent of the invention for homologous recombination, to replace DNA fragments and as antiviral agents. For example, one method of in vivo homologous recombination in a cell to replace a desired region of DNA is accomplished by reacting a DNA having a target cleavage site at or near the region with a nucleic acid cleavage agent of the invention, the agent being specific for the desired target cleavage site, for a time and under conditions to introduce a nick in the DNA at the desired site and introducing a DNA fragment comprising a sequence homologous to the region at or around the site into said cell to obtain homologous recombination. The nucleic acid cleavage agent can be introduced into the cell prior to or simultaneous with introducing the DNA fragment. Likewise the cleavage agent can already be encoded in the cell.

When used as an antiviral agent, the nucleic acid cleavage agent of the invention has specificity for a target cleavage site on a viral nucleic acid and can be introduced as the protein, a nucleic acid or a recombinant expression vector. The antiviral agent can, optionally, be mixed with a pharmaceutically-acceptable carrier. Hence, the invention provides a method of treating a viral disease by administering an antiviral agent of the invention to a patient in need of treatment for a time and in an amount to cleave viral nucleic acid in said patient. Reducing viral load should ameliorate the symptoms and or full course of the disease.

BRIEF DESCRIPTION OF THE DRAWINGS

FIG. 1 discloses SEQ ID NOS 13, 13, 14 and 1, respectively, in order of appearance.

FIG. 2 discloses SEQ ID NOS 1 and 14, respectively, in order of appearance.

BEST MODE FOR CARRYING OUT THE INVENTION

The nucleic acid cleaving agent of the present invention can specifically cleave a target cleavage site in a nucleic acid, preferably a unique site in a large DNA or RNA. The nucleic acid cleaving agent of the present invention comprises (1) a nucleic acid cleaving moiety, and (2) at least two zinc finger proteins bound to the nucleic acid cleaving moiety, wherein at least one of the zinc finger proteins is capable of specifically binding to a nucleotide sequence located upstream from the target cleavage site, and at least one of the remaining zinc finger proteins is capable of specifically binding to a nucleotide sequence located downstream from the target cleavage site.

Figure 1:
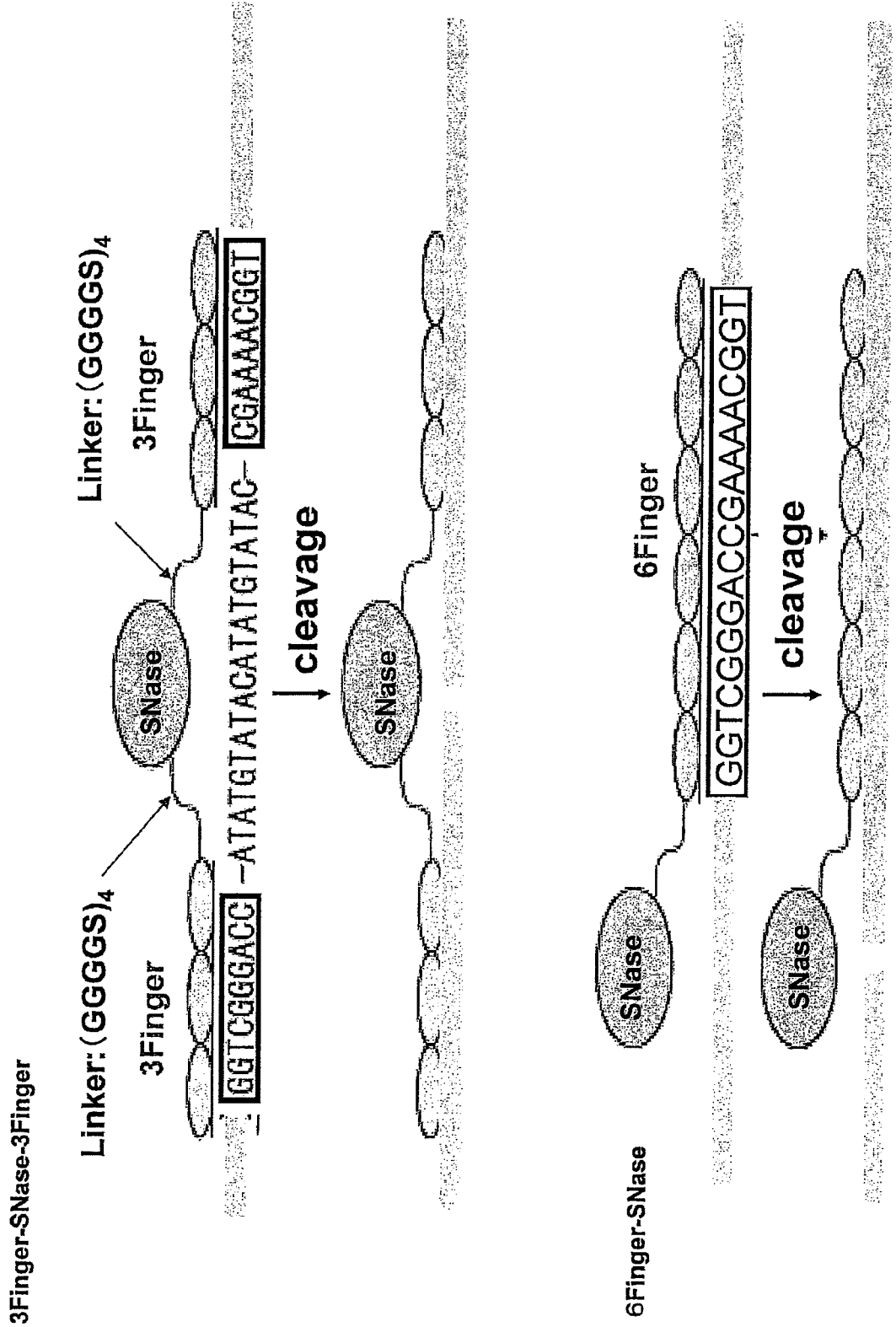
FIG. 1 is a schematic diagram showing the action of the nucleic acid cleaving agent of the present invention. In the figures, each right end of the 3Fingers or 6Finger indicates N-terminus, and each left end of the 3Fingers or 6Finger indicates C-terminus. In the upper figure, the 3Finger depicted in the right side, which is bound to the linker (GGGGS)$_4$ (SEQ ID NO: 13) at the C-terminus, has the amino acid sequence of from amino acid number 1 to 84 of the amino acid sequence indicated in FIG. 1-c of Journal of Virology, Vol.80, No.11, pp.5405-5412, 2006, and the left side 3Finger, which is bound to the linker (GGGGS)$_4$ (SEQ ID NO: 13) at the N-terminus, has the amino acid sequence of from amino acid number 85 to 168 of the same amino acid sequence.

One example of a preferred embodiment of the nucleic acid cleaving agent of the present invention is shown in FIG. 1. In this preferred embodiment, the target nucleic acid is DNA, and two independent zinc finger proteins bind to the DNA cleaving portion. Hereafter, the present invention will be specifically explained on the basis of this preferred embodiment. However, the present invention is not limited to this preferred embodiment.

In FIG. 1, the ellipse in the center represents a nucleic acid cleaving moiety, and SNase is shown as a preferred embodiment thereof. Two independent zinc finger proteins (each having three zinc finger domains) bind to the nucleic acid cleaving moiety, one of them specifically binds to a DNA sequence upstream a target cleavage site (the binding constant of this zinc finger protein for the DNA is designated as "K1"), and the other one specifically binds to a DNA sequence downstream the target cleavage site (the binding constant of this zinc finger protein for the DNA is designated as "K2"). The binding constant of this nucleic acid cleaving agent for the DNA is thus K1×K2. This nucleic acid cleaving agent strongly binds to the DNA by the six zinc finger domains.

When the target cleavage site is cleaved by the nucleic acid cleaving moiety of the nucleic acid cleaving agent, the DNA is separated into two cleavage products, and each cleavage product is bound with one zinc finger protein. Since the binding constants of the zinc finger proteins for these cleavage products are K1 or K2, and are much lower than the binding constant of the nucleic acid cleaving agent for the uncleaved DNA (K1×K2), each of the zinc finger proteins dissociates from each cleavage product. Thus, two, unbound cleavage products are produced as well as a free nucleic acid cleaving agent, i.e., the agent not bound with the cleavage products. The free nucleic acid cleaving agent can again bind to the target nucleic acid and cleave the target cleavage site under the same process as described above. This binding-cleavage-dissociation cycle can continue in a catalytic manner.

Examples of the target nucleic acid of the nucleic acid cleaving agent of the present invention include DNA and RNA, and DNA can be preferably used as the target nucleic acid. Large DNA, such as genomic DNA, cosmids, chromosomal DNA, and large viral DNA can be cleaved at single sites since the nucleic acid cleaving agents of the invention can be designed for unique target sites on such large DNA (or RNA molecules).

The type of the nucleic acid cleaving moiety is not particularly limited so long as a substance having a nucleic acid cleaving activity is chosen, and any substances having a nucleic acid cleaving activity such as nucleic acid cleaving enzymes such as DNA cleaving enzymes and RNA cleaving enzymes, metal complexes having a nucleic acid cleaving activity and organic ligands exhibiting a nucleic acid cleaving activity by coordination of a metal can be used. For example, a whole nucleic acid cleaving enzyme or a nucleic acid cleaving domain thereof as a part of the full-length of the enzyme can be used. In addition to naturally-occurring nucleic acid cleaving enzymes, e.g., restriction enzymes, SNase, and the like, such nucleic acid cleaving enzymes altered by genetic engineering techniques or other techniques can also be used. A nucleic acid cleaving domain in a nucleic acid cleaving enzyme can be easily identified in a conventional manner by those skilled in the art and can be easily obtained by genetic engineering techniques. As the nucleic acid cleaving enzyme, Staphylococcal nuclease (SNase) having a cleaving activity for DNA or RNA or a nucleic acid cleaving domain thereof, a mutant SNase containing substitution, insertion, or deletion of one or more constituent amino acid residues, preferably several residues, of the SNase and the like can be used, but the nucleic acid cleaving moiety is not limited to these examples. Further, as the nucleic acid cleaving moiety, metal complexes having a nucleic acid cleaving activity and organic ligands exhibiting a nucleic acid cleaving activity by coordination of a metal can also be used. Metal complexes for this purpose include, but are not limited to, cerium complexes and the like (for example, refer to Japanese Patent Unexamined Publication No. 2005-143484 and the like). These complexes can thus be used as the nucleic acid cleaving moiety.

In the nucleic acid cleaving agent of the present invention, the nucleic acid cleaving moiety need not to have a sequence-specific cleaving activity for a sequence of a target cleavage site, and may have a random cleaving activity for a nucleic acid such as DNA and RNA. The target cleavage site in a nucleic acid can be suitably determined depending on types of zinc finger proteins to be used (specificity for nucleotide sequences around the target cleavage site and the like) and locations of two zinc finger proteins (distance between at least two zinc finger proteins across the target cleavage site and the like). At least two zinc finger proteins are chosen so that at least one of the zinc finger proteins binds upstream (on the 5' side), and at least one of the remaining zinc finger proteins binds downstream (on the 3' side) from the target cleavage site in a sequence-specific manner. Preferably, two zinc finger proteins are chosen so that one of them can sequence-specifically bind upstream from the target cleavage site, and the other one can sequence-specifically bind downstream therefrom.

As a preferred embodiment of the present invention, a nucleic acid cleaving agent containing two zinc finger proteins is depicted schematically in FIG. 1. Each of the nucleotide sequences recognized by the zinc finger proteins consist of 10 nucleotides and each zinc finger protein has three zinc finger domains with a binding constant of K1 or K2, respectively. The nucleotides between the binding sites of the zinc finger proteins (i.e., the central site), can be suitably chosen depending on a mode of nucleic acid cleavage and size of the nucleic acid cleaving moiety. Preferably these sequence consists of about 5 to 50 nucleotides, more preferably about 10 to 40 nucleotides, still more preferably about 15 to 30 nucleotides. One nucleotide or several continuous nucleotides constituting the central site can be chosen as the target cleavage site. For example, when the central site constitutes 20 nucleotides, the target cleavage site can be designed so that, for example, the sequence can be cleaved between the 10th and 11th nucleotides by suitably adjusting the locations of the two zinc finger proteins.

In order to efficiently attain such design, the nucleic acid cleaving moiety and the zinc finger proteins are preferably bound (covalently joined) by means of a suitable linker, for example, an arbitrary linker such as a linker consisting of one amino acid residue, an oligopeptide linker or a polypeptide linker. The oligopeptide linker or polypeptide linker is preferably an oligopeptide linker having from about 2 to about 200 amino acid residues, preferably from about 3 to about 100 amino acid residues, more preferably from about 5 to about 50 amino acid residues. One amino acid residue can also be used as the linker. In addition to peptide linkers, synthetic linkers such as alkylene chains and polyethylene glycol chains, sugar chains, and the like may also be used as the linker. By suitably choosing type and length of the linker that connect the nucleic acid cleaving moiety and each of two zinc finger proteins, the nucleic acid cleaving moiety can be located at a desired position relative to the central site between the recognition nucleotide sequences to which the two zinc finger proteins bind. Linkers for connecting at least two zinc finger proteins are described in, for example, International Patent Application Unexamined Publication in Japanese (Kohyo) No. 2002-505111 and the like, and these linkers can also be used.

The nucleic acid cleaving moiety and the zinc finger proteins can also bind each other non-covalently by each protein having a region with sufficient affinity for a region or portion of the nucleic acid cleaving moiety so that such regions of affinity do not interfere with the activity of each domain and so that the affinity of the domains is sufficiently stronger to maintain the complex under the cleavage reaction conditions. For example, strep-avidin or biotin-avidin complexes suitably arranged (e.g., biotin on the protein, avidin on the moiety) can serve as binding partners. Preferably the binding partners for one zinc finger protein to the nucleic acid cleaving moiety is different from that of the other zinc finger protein for the nucleic acid cleaving moiety.

For the zinc finger proteins, besides a full-length polypeptide of a zinc finger protein containing several zinc finger domains (in the specification, "zinc finger domain" means a domain constituting a nucleic acid binding site, preferably a DNA binding site, existing in a zinc finger protein, and may also be simply referred to as "finger", and a zinc finger protein typically has two, three, four or six zinc finger domains), a zinc finger partial polypeptide as a partial sequence thereof, and the like can also be used. In addition to naturally occurring zinc finger proteins, altered zinc finger proteins including substitution, insertion, or deletion of one or several amino acid residues, chimeric zinc finger proteins comprising a combination of zinc finger domains of two or more types of zinc finger proteins, and the like can also be used. Further, these zinc finger proteins may be bound with one or more nucleic acid binding domains derived from other proteins. Examples of such nucleic acid binding domains include DNA binding domains of proteins that can bind to nucleic acids such as restriction enzymes and nuclear hormone receptors, and the like.

A zinc finger protein having specificity for a certain specific nucleotide sequence can be prepared by suitably modifying or altering a zinc finger domain of a zinc finger protein, and such a technique is well known to those skilled in the art. It is known that zinc finger proteins that can bind to RNA, besides DNA, can be prepared. It is recognized that, in theory, zinc finger proteins can be designed so that they have specificity for an arbitrary desired sequence on a genome, and therefore, it is easy for those skilled in the art to design suitably modified or altered zinc finger proteins depending on a desired cleavage site.

For designing the nucleic acid cleaving agent of the present invention, when the target nucleic acid is a genomic DNA, for example, the target cleavage site is first identified on a genome, and a nucleotide sequence containing that site and having a suitable length (for example, about 10 to 30 nucleotides) is determined as sequence for the central site. Then, zinc finger proteins are designed that can specifically bind to a nucleotide sequence (for example, about 8 to 12 nucleotides) on the upstream side of the central site sequence and a nucleotide sequence (for example, about 8 to 12 nucleotides) on the downstream side thereof. Further, a suitable nucleic acid cleaving moiety (for example, SNase and the like) is chosen, and at least two, preferably two, zinc finger proteins and the nucleic acid cleaving moiety are bound preferably by means of suitable linkers (peptide linkers comprising about several to 30 amino acid residues and the like) so that the nucleic acid cleaving domain can approach the target cleavage site. The linkers for binding the zinc finger proteins can be the same or different. One example of the method for producing the nucleic acid cleaving agent of the present invention will be specifically explained in the example of the specification. By referring to the above general explanations and the specific explanations in the example, those skilled in the art can chose suitable materials and easily produce the nucleic acid cleaving agent of the present invention, if necessary, by adding suitable modification or alteration to the specific method disclosed in the example.

The nucleic acid cleaving agent of the present invention can be used to cleave a desired target cleavage site in DNA or RNA, in the same manner as, for example, restriction enzymes used in genetic engineering. The nucleic acid cleaving agent of the present invention is further characterized to be also applicable to large nucleic acids, preferably large DNA. For example, it is known that when a nick is introduced into a genomic DNA, homologous recombination more readily occurs at that site. By introducing a cleavage at a desired site on a genome by using the nucleic acid cleaving agent of the present invention and then introducing a DNA fragment, which contains a sequence homologous to the region and with which the region is desired to be replaced, into a cell from the outside, homologous recombination is achievable to freely manipulate genomic information.

Further, the nucleic acid cleaving agent of the present invention can also be used as, for example, a medicament for regenerative medicine or gene therapy, antiviral agent, or the like. For example, two different sites on a genome can be cleaved by using two types of different nucleic acid cleaving agents in combination, and a genome region between the two sites can be removed by homologous recombination. For example, it becomes possible to remove an HIV genome incorporated into a genome of an HIV patient by such technique. Further, a sequence specific solely to a DNA of a virus that invades living bodies is targeted to cleave the nucleic acid, viral infection can also be prevented. A sequences specific solely to viral DNA, but not in human genomes include the viral DNA of DNA viruses per se as well as DNA transcribed from RNA viruses.

EXAMPLE

The present invention is explained more specifically by referring to the example. However, the scope of the present invention is not limited to the following example.

Example 1

A. Materials and Methods
(1) Cloning
(a) 6-Finger-SNase

First, a DNA fragment encoding (GGGGS)$_4$ (SEQ ID NO: 13)-SNase-(GGGGS)$_4$ (SEQ ID NO: 13) (G: Gly, S: Ser) was prepared by PCR and cloned in an *Escherichia coli* expression vector pET-21a (Novagen). A DNA fragment encoding an artificial DNA-binding protein, 6-Finger, containing six zinc finger domains recognizing 5'-GGTCGGGAC-CGAAAACGGT-3' (SEQ ID NO: 1) was cloned on the N-terminus side of the first (GGGGS)$_4$ (SEQ ID NO: 13) peptide linker of the vector pET-SNase to prepare an *Escherichia coli* vector expressing a fusion protein consisting of 6-Finger and SNase bound by means of a peptide linker (6-Finger-SNase).
(b) 3-Finger-SNase-3-Finger (3+3-Finger-SNase)

The vector for this protein was prepared by two steps. First, a DNA fragment encoding an artificial DNA-binding protein containing three zinc finger domains recognizing 5'-CGAAAACGGT-3' (SEQ ID NO: 2), 3-Finger, was cloned on the N-terminus side of the first (GGGGS)$_4$ (SEQ ID NO: 13) peptide linker of the aforementioned vector pET-SNase. Then, a DNA fragment encoding an artificial DNA-binding protein recognizing 5'-GGTCGGGACC-3' (SEQ ID NO: 3), a second 3-Finger, was cloned on the C-terminus side of the second (GGGGS)$_4$ (SEQ ID NO: 13) peptide linker of the vector to prepare an *Escherichia coli* vector expressing a fusion protein comprising the two 3-Fingers each bound to SNase by means of a peptide linker (3+3-Finger-SNase).
(2) Preparation of Fusion Protein Each of the two fusion proteins was expressed by using an *Escherichia coli* strain, BL21(DE3)pLysS (Novagen). Cells of the *Escherichia coli* strain were cultured at 37° C., and when the value of OD$_{600}$ reached 0.6, 1 mM IPTG was added to induce expression of the fusion protein. After three hours of the culture, *Escherichia coli* cells were collected and disrupted by ultrasonication, and the expressed fusion protein was purified by using a Bio-Rex 70 cation-exchange resin column (Bio-Rad). Purity of the resulting fusion protein was 95% or higher as determined by SDS-PAGE analysis. Concentration of each protein was determined by using Protein Assay ESL (Roche Molecular Biochemicals).

(3) Preparation of Target DNA (a) For 6-Finger-SNase

A double-stranded DNA having the recognition sequence of 6-Finger, 5'-GGTCGGGACCGAAAACGGT-3' (SEQ ID NO: 1), was cloned at the HindIII/EcoRI site of pBluescriptll KS+(Stratagene). This vector was purified by large scale culture of Escherichia coli. This vector was cleaved with XmnI to obtain linear DNA, and the DNA was purified by phenol extraction.

(b) For 3+3-Finger-SNase

A double-stranded DNA comprising the sequences 5'-GGTCGGGACC-3' (SEQ ID NO: 3) and 5'-CGAAAACGGT-3' (SEQ ID NO: 2), which are recognized by the two 3-Fingers ZFP1 and ZFP2, respectively, were joined via a spacer DNA, 5'-ATATGTATAC ATATGTATAC-3' (SEQ ID NO: 7), and cloned at the HindIII/EcoRI site in pBluescriptII KS+(Stratagene). This vector was purified by large scale culture of Escherichia coli, and cleaved with XmnI to obtain linear DNA which was purified by phenol extraction.

(4) Cleavage Reaction

Figure 2:
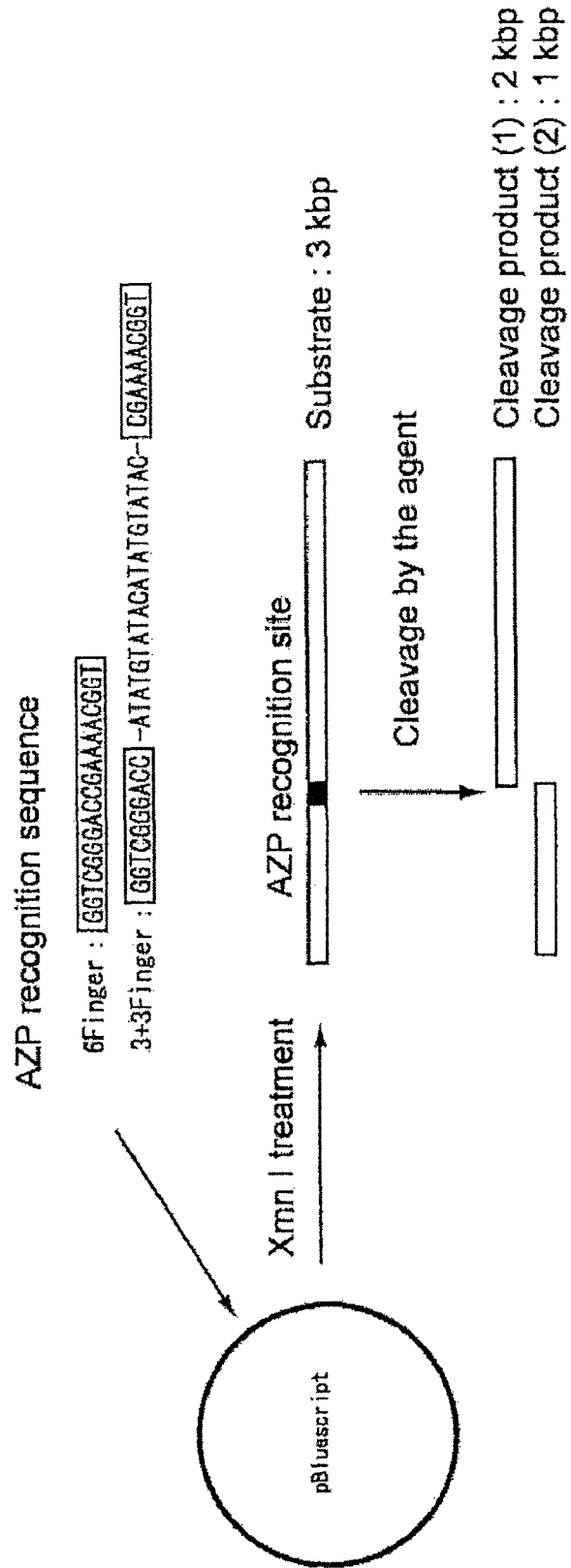
FIG. 2 schematically depicts the cleavage reaction performed in Example 1.

To 4 µl of $H_2O$ was added 10× Reaction Buffer (0.5 M Tris-HCl, pH 7.5, 1 M NaCl), 1 µl of tRNA (10 µg/µl), 1 µl of the target linear DNA and 2 µl of the appropriate fusion protein, and left on ice for 10 minutes. Then, 1 µl of 100 mM $CaCl_2$ was added to the mixture, and a reaction was allowed to proceed at 37° C. for 30 minutes. After completion of the reaction, the proteins were removed by phenol extraction, and the resulting nucleic acid cleavage reaction products were analyzed by 0.8% agarose gel electrophoresis. The outline of the cleavage reaction is shown in FIG. 2.

B. Results

Figure 3:
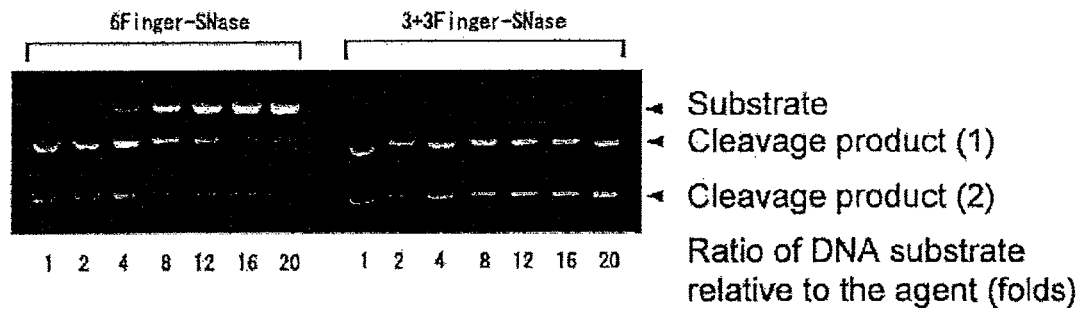
FIG. 3 is a photograph of an agarose gel showing the cleavage reaction products from Example 1. In the figure, the numerals of 1 to 20 denote ratios (-folds) of DNA substrate relative to the nucleic acid cleaving agent.
Figure 4:
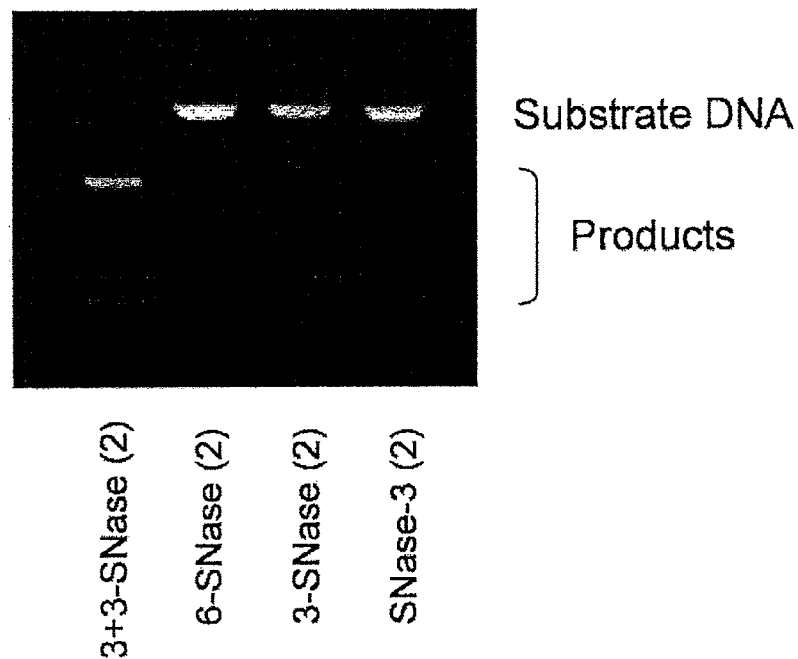
FIG. 4 is a photograph of an agarose gel showing the cleavage reaction products from Example 2. In this experiment, a 200-fold excess of the DNA substrate relative to the nucleic acid cleaving agent was used.
Figure 5:
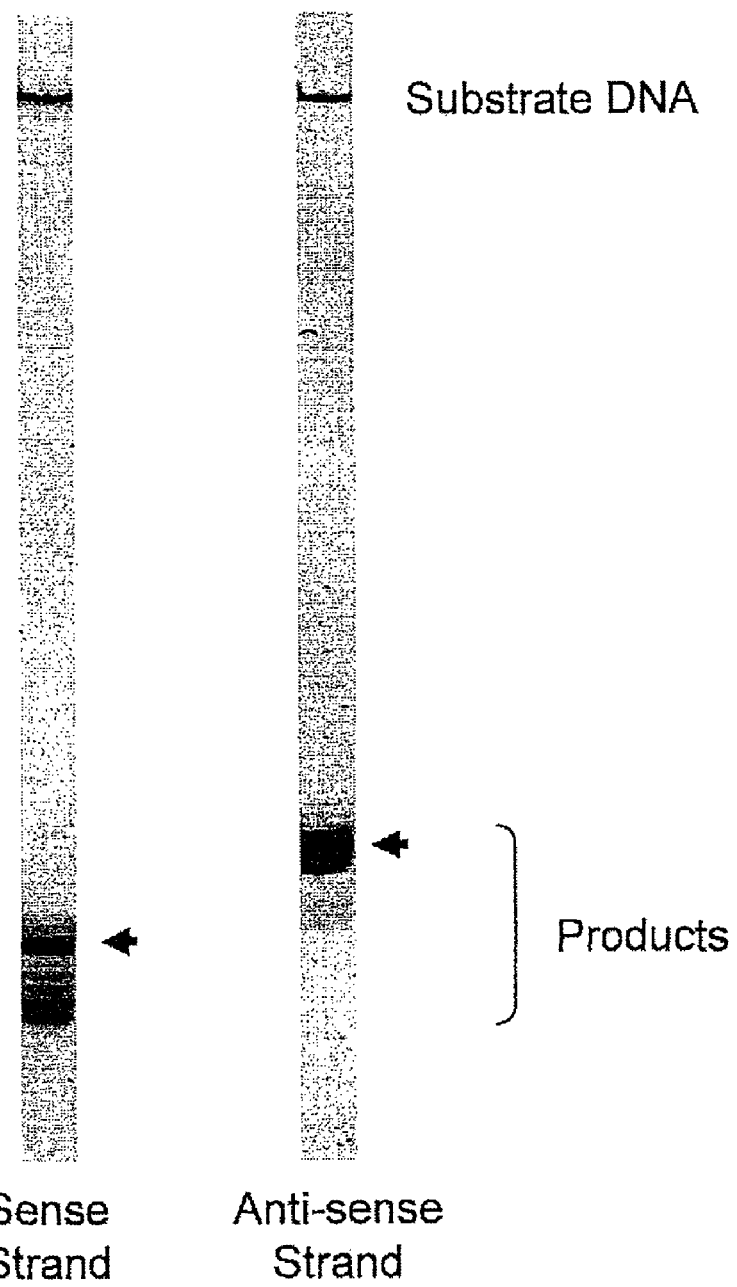
FIG. 5 Fig. is a photograph of a denaturing gel showing the cleavage site of each DNA strand of the substrate from Example 2.

The results are shown in FIG. 3. The 6-Finger-SNase and 3+3-Finger-SNase cleaved the substrate DNA at the target cleavage sites in a site-specific manner. Further, the 3+3-Finger-SNase, a nucleic acid cleaving agent of the invention, had much higher cleaving activity for high concentrations of nucleic acid target than did the 6-Finger-SNase. The reason is considered as follows: When a large amount of DNA substrate was subjected to cleavage, the 6-Finger-SNase remained bound to one of DNA cleavage products after the cleavage, and the amount of the nucleic acid cleaving agent became insufficient for excess DNA, resulting in low cleavage efficiency. On the other hand, turnover of 3+3-Finger-SNase of the present invention was achieved because the nucleic acid cleaving agent was became free, i.e., regenerated, by dissociating from the DNA cleavage products after the cleavage, and resulting in a free cleaving agent that could bind again to the substrate nucleic acid. The 3+3-Finger-SNase thus exhibits the cleaving activity in a catalytic manner.

Further, two controls were prepared, namely ZFP1-SNase (3-Finger-SNase) in which ZFP1 has a 3-Finger protein recognizing the sequence 5'-GGTCGGGACC-3' (SEQ ID NO: 3) bound to SNase on the N-terminus side, and SNase-ZFP2 (3-Finger-SNase) in which ZFP2 has a 3-Finger protein recognizing the sequence 5'-CGAAAACGGT-3' (SEQ ID NO: 2) bound to SNase on the C-terminus side. The target cleaving activities thereof were examined under the same conditions as described above. For ZFP1-SNase, no cleavage activity was observed, whereas for SNase-ZFP2, weak activity occurred but no turnover was observed.

Example 2

A. Materials and methods (1) Cloning (a) 6-Finger-SNase (2)

First, a DNA fragment encoding $(GGGGS)_4$ (SEQ ID NO: 13)-SNase-$(GGGGS)_4$ (SEQ ID NO: 13) (G: Gly, S: Ser) was prepared by PCR and cloned in an Escherichia coli expression vector pET-21a (Novagen). A DNA fragment encoding an artificial DNA-binding protein, 6-Finger (2), containing six zinc finger domains recognizing 5'-GGTCGGGACGT-TGCGGGAT-3' (SEQ ID NO: 6) was cloned on the N-terminus side of the first $(GGGGS)_4$ (SEQ ID NO: 13) peptide linker of the vector pET-SNase to prepare an Escherichia coli vector expressing a fusion protein consisting 6-Finger and SNase bound by means of a peptide linker (6-Finger-SNase (2)).

(b) 3-Finger-SNase-3-Finger (2) (3+3-Finger-SNase (2))

The vector for this protein was prepared by two steps. First, a DNA fragment encoding an artificial DNA-binding protein containing three zinc finger domains recognizing 5'-GT-TGCGGGAT-3' (SEQ ID NO: 5), 3-Finger, was cloned on the N-terminus side of the first $(GGGGS)_4$ (SEQ ID NO: 13) peptide linker of the aforementioned vector pET-SNase. Then, a DNA fragment encoding an artificial DNA-binding protein recognizing 5'-GGTCGGGACC-3' (SEQ ID NO: 3), a second 3-Finger, was cloned on the C-terminus side of the second $(GGGGS)_4$ (SEQ ID NO: 13) peptide linker of the vector to prepare an Escherichia coli vector expressing a fusion protein comprising the two 3-Fingers each bound to SNase by means of a peptide linker (3+3-Finger-SNase (2)).

(c) 3-Finger-SNase (2)

A DNA fragment encoding an artificial DNA-binding protein, 3-Finger, containing six zinc finger domains recognizing 5'-GTTGCGGGAT-3' (SEQ ID NO: 5) was cloned on the N-terminus side of the first $(GGGGS)_4$ (SEQ ID NO: 13) peptide linker of the vector pET-SNase to prepare an Escherichia coli vector expressing a fusion protein consisting 6-Finger and SNase bound by means of a peptide linker.

(d) SNase-3-Finger (2)

A DNA fragment encoding an artificial DNA-binding protein, 3-Finger, containing six zinc finger domains recognizing 5'-GGTCGGGACC-3' (SEQ ID NO: 3) was cloned on the C-terminus side of the second $(GGGGS)_4$ (SEQ ID NO: 13) peptide linker of the vector pET-SNase to prepare an Escherichia coli vector expressing a fusion protein consisting 6-Finger and SNase bound by means of a peptide linker.

(2) Preparation of Fusion Protein

Each of the two fusion proteins was expressed by using an Escherichia coli strain, BL21(DE3)pLysS (Novagen). Cells of the Escherichia coli strain were cultured at 37° C., and when the value of $OD_{600}$ reached 0.6, 1 mM IPTG was added to induce expression of the fusion protein. After three hours of the culture, Escherichia coli cells were collected and disrupted by ultrasonication, and the expressed fusion protein was purified by using a Bio-Rex 70 cation-exchange resin column (Bio-Rad). Purity of the resulting fusion protein was 95% or higher as determined by SDS-PAGE analysis. Concentration of each protein was determined by using Protein Assay ESL (Roche Molecular Biochemicals).

(3) Preparation of Target DNA (a) For 6-Finger-SNase

A double-stranded DNA having the recognition sequence of 6-Finger, 5'-GGTCGGGACGTTGCGGGAT-3' (SEQ ID NO: 6), was cloned at the HindIII/EcoRI site of pBluescriptII KS+(Stratagene). This vector was purified by large scale culture of *Escherichia coli*. This vector was cleaved with XmnI to obtain linear DNA, and the DNA was purified by phenol extraction.

(b) For 3+3-Finger-SNase (2), 3-Finger-SNase (2), and SNase-3-Finger (2)

A double-stranded DNA comprising the sequences 5'-GGTCGGGACC-3' (SEQ ID NO: 3) and 5'-GTTGCGG-GAT-3' (SEQ ID NO: 5), which are recognized by the two 3-Fingers ZFP3 and ZFP2, respectively, were joined via a spacer DNA, 5'-ATATGTATAC ATATGTATAC-3' (SEQ ID NO: 7), and cloned at the HindIIIEcoRI site in pBluescriptII KS+(Stratagene). This vector was purified by large scale culture of *Escherichia coli*, and cleaved with XmnI to obtain linear DNA which was purified by phenol extraction.

(4) Cleavage Reaction; DNA: ZFP-SNase=2000:1

To 34 µl of H$_2$O was added 20 µl of 10× Reaction Buffer (0.5 M Tris-HCl, pH 7.5, 1 M NaCl), 1 µl of tRNA (10 µg/µl), 123 µl of the target DNA plasmid (1.63 µg/µl) and 2 µl of the appropriate fusion protein (25 nM), and left on ice for 10 minutes. Then, 20 µl of 100 mM CaCl$_2$ was added to the mixture, and a reaction was allowed to proceed at 37° C. for 300 minutes. After completion of the reaction, the reaction mixture was digested with Xmn I (200 units) at 37° C. for 60 minutes, and then the proteins were removed by phenol extraction, and 0.1 µg of the resulting nucleic acid cleavage reaction products were analyzed by 0.8% agarose gel electrophoresis.

B. Results

The results are shown in Figure A. 3+3-Finger-SNase (2) cleaved a large amount (200 µg) of the substrate DNA at the target cleavage sites in a site-specific manner. In this experiment, an amount of DNA used is 200 fold as high as that of each SNase derivative. Under the same condition, any turnover of DNA cleavage reaction was not observed for other three SNase derivatives, 6-Finger-SNase (2), 3-Finger-SNase (2), and SNase-3-Finger (2).

Example 3

A. Materials and Methods
(1) Preparation of Target DNA Labeled with Alexa680
(a) DNA labeled at a 5'-terminus of a sense strand A double-stranded 200-bp DNA having the recognition sequence of 3+3-Finger-SNase (2), 5'-GGTCGGGACC ATATGTATAC ATATGTATAC GTTGCGGGAT-3' (SEQ ID NO: 8), were amplified using the plasmid as a template by PCR with primers 5'-Alexa680-CTGGGTACCGGGC-CCCCCCTCGAGGTCGAC-3' (SEQ ID NO: 9) and 5'-TTG-TAAAACGACGGCCAGTGAGCGCGCGTA-3' (SEQ ID NO: 10). The resulting PCR product was purified with the QIAquick PCR Purification Kit (Qiagen).

(b) DNA labeled at a 5'-terminus of an anti-sense strand

A double-stranded 200-bp DNA having the recognition sequence of 3+3-Finger-SNase (2), 5'- GGTCGGGACC ATATGTATAC ATATGTATAC GTTGCGGGAT-3' (SEQ ID NO: 8), were amplified using the plasmid as a template by PCR with primers 5'-TCACACAGGAAACAGCTATGAC-CATGATTA-3' (SEQ ID NO: 11) and 5'-Alexa680-GGCG-GCCGCTCTAGAACTAGTGGATCCCCC-3' (SEQ ID NO: 12). The resulting PCR product was purified with the QIAquick PCR Purification Kit.

(2) Cleavage Reaction: Analysis on a 6% Denaturing Gel

To 4 µl of H$_2$O was added 1 µl of 10× Reaction Buffer (0.5 M Tris-HCl, pH 7.5, 1 M NaCl), 1 µl of tRNA (10 µg/µl), 1 µl of the target DNA (0.1 µg/µl) containing a labeled 5'-terminus at a sense strand or at an anti-sense one and 2 µl of the appropriate fusion protein (25 nM), and left on ice for 10 minutes. Then, 1 µl of 100 mM CaCl$_2$ was added to the mixture, and a reaction was allowed to proceed at 37° C. for 30 minutes. After completion of the reaction, the proteins were removed by phenol extraction, and the resulting nucleic acid cleavage reaction products were analyzed by 6% denaturing gel electrophoresis.

B. Results

The results are shown in Figure B. As shown in Figure B, 3+3-Finger-SNase (2) cleaved the target DNA mainly at the single site of each DNA strand.

Industrial Applicability

The nucleic acid cleaving agent of the present invention has a cleaving activity specific to a desired nucleotide sequence in a large nucleic acid such as genomic DNAs, preferably unique sites on such DNA. The nucleic acid cleaving agent of the present invention exhibits the desired cleaving activity as a sole molecule and efficiently cleaves nucleic acids on the basis of catalytic turnover.

The invention claimed is:

1. A nucleic acid cleaving agent capable of specifically cleaving a target cleavage site in a nucleic acid which comprises:
   (1) a nucleic acid cleaving moiety comprising a) an amino acid sequence encoding a polypeptide having a nuclease activity or b) an amino acid sequence encoding a peptide that is capable of binding to a metal complex and acting as a nucleic acid cleaving moiety upon binding, and
   (2) at least two zinc finger proteins bound to said nucleic acid cleaving moiety, wherein at least one of said zinc finger proteins is capable of specifically binding to a nucleotide sequence located upstream from said target cleavage site, and at least one of the remaining zinc finger proteins is capable of specifically binding to a nucleotide sequence located downstream from the target cleavage site,
   wherein each of the zinc finger proteins are independently bound to the nucleic acid cleaving moiety by a peptide linker and wherein said peptide linker is an oligopeptide linker independently containing 5 to 50 amino acid residues,
   and wherein the structural order of components of the nucleic acid cleaving agent is zinc finger protein-peptide linker-nucleic acid cleaving moiety-peptide linker-zinc finger protein.

2. The nucleic acid cleaving agent according to claim 1, wherein two (2) zinc finger proteins are bound to the nucleic acid cleaving moiety.

3. The nucleic acid cleaving agent according to claim 2, wherein the total number of zinc finger domains contained in the two zinc finger proteins is from 4 to 8.

4. The nucleic acid cleaving agent according to claim 2, wherein each zinc finger protein comprises four or less zinc finger domains.

5. The nucleic acid cleaving agent according to claim 2, wherein each zinc finger protein comprises three zinc finger domains.

6. The nucleic acid cleaving agent according to claim 1, wherein the nucleic acid is DNA or RNA.

7. The nucleic acid cleaving agent according to claim 1, wherein the nucleic acid cleaving moiety is a nucleic acid cleaving enzyme or a nucleic acid cleaving domain thereof, a metal complex having a nucleic acid cleaving activity, or an organic ligand that has nucleic acid cleaving activity upon coordination of a metal.

8. The nucleic acid cleaving agent according to claim 1, wherein the nucleic acid cleaving moiety is Staphylococcal nuclease (SNase), a nucleic acid cleaving domain thereof, or an altered protein thereof having nucleic acid cleaving activity.

9. An isolated nucleic acid comprising a nucleotide sequence encoding the nucleic acid cleaving agent according to claim 1.

10. The nucleic acid according to claim 9, wherein the nucleic acid is DNA or RNA.

11. A recombinant expression vector comprising the nucleic acid according to claim 9.

12. An isolated host cell comprising the recombinant expression vector of claim 11.

13. A method of producing a nucleic acid cleavage agent which comprises (a) culturing the host cell of claim 12 for a time and under conditions to express said agent; and (b) recovering said agent.

14. A method of site-specifically cleaving a nucleic acid which comprises
   (a) reacting a nucleic acid having a target cleavage site with a nucleic acid cleavage agent according to claim 1 for a time and under conditions to cleave said site, said agent being specific for said site.

15. The method of claim 14, wherein said cleavage proceeds catalytically.

16. The method of claim 14, wherein said target cleavage site is a unique site on a genomic DNA.

17. An antiviral agent comprising the nucleic acid cleavage agent according to claim 1, said agent having specificity for a target cleavage site on a viral nucleic acid, and a pharmaceutically acceptable carrier.

18. A method of treating a viral disease, which comprises administering the antiviral agent of claim 17 to a patient in need of said treatment for a time and in an amount to cleave viral nucleic acid in said patient.

* * * * *